(12) United States Patent
Park et al.

(10) Patent No.: US 11,781,951 B2
(45) Date of Patent: Oct. 10, 2023

(54) KIT FOR COLLECTING BIO-SAMPLES USING A COLLECTION ROD

(71) Applicant: BODITECH MED INC., Gangwon-do (KR)

(72) Inventors: Sang Hyun Park, Seoul (KR); Byeong Chul Kim, Gangwon-do (KR)

(73) Assignee: BODITECH MED INC., Gangwon-Do (KR)

( * ) Notice: Subject to any disclaimer, the term of this patent is extended or adjusted under 35 U.S.C. 154(b) by 0 days.

(21) Appl. No.: 17/734,171

(22) Filed: May 2, 2022

(65) Prior Publication Data

US 2022/0357241 A1 Nov. 10, 2022

(30) Foreign Application Priority Data

May 10, 2021 (KR) .................. 10-2021-0059787

(51) Int. Cl.
*G01N 1/10* (2006.01)
*G01N 1/02* (2006.01)
*B01L 3/00* (2006.01)
*A61B 10/00* (2006.01)
*A61B 5/08* (2006.01)

(52) U.S. Cl.
CPC ......... *G01N 1/10* (2013.01); *G01N 2001/028* (2013.01); *G01N 2001/1056* (2013.01)

(58) Field of Classification Search
CPC ............... G01N 1/10; G01N 2001/028; G01N 2001/1056; B01L 2300/028; B01L 2300/0681; B01L 3/5029; B01L 3/50825; A61B 10/0051; A61B 5/08; A61B 10/0096; A61B 2010/009
See application file for complete search history.

(56) References Cited

U.S. PATENT DOCUMENTS

| 5,624,554 A | 4/1997 | Faulkner et al. |
| 2006/0115385 A1 | 6/2006 | Jon Meyer et al. |
| 2010/0215548 A1* | 8/2010 | De Luca ............ A61B 10/0038 422/550 |
| 2011/0048981 A1 | 3/2011 | Okumura et al. |
| 2017/0224315 A1 | 8/2017 | Bastia |

FOREIGN PATENT DOCUMENTS

| JP | 4961029 B2 | 3/2012 |
| JP | 5065503 B2 | 8/2012 |
| JP | 5379061 | 10/2013 |
| JP | 2013217707 A | 10/2013 |
| KR | 200461199 Y1 | 7/2012 |
| KR | 102211288 B1 | 2/2021 |
| WO | 2011095559 A1 | 8/2011 |

OTHER PUBLICATIONS

Extended European Search Report, dated Sep. 1, 2022.

* cited by examiner

*Primary Examiner* — Herbert K Roberts
*Assistant Examiner* — Anthony W Megna Fuentes
(74) *Attorney, Agent, or Firm* — Levenfeld Pearlstein, LLC

(57) ABSTRACT

The present invention relates to a kit with which a user can conveniently and hygienically collect bio-samples using a collecting rod. A collection kit for collecting a bio-sample using a collection rod according to the present invention comprises: a cap on the lower part of the central part of which a filter is detachably mounted, wherein a cover is formed on the upper part of the filter; a collection rod having a collection unit and a handle part; and a tube fastened with the cap and for accommodating the extraction solution.

7 Claims, 7 Drawing Sheets

KIT FOR COLLECTING BIO-SAMPLES USING A COLLECTION ROD

TECHNICAL FIELD

The present invention relates to a kit for collecting bio-samples, and more particularly, to a kit with which a user can conveniently and hygienically collect bio-samples using a collecting rod.

BACKGROUND ART

In general, kits for collecting Covid-19 specimens using a swab (or a collection rod) are available for nasal use and oral use.

In the field inspection using the nasal collection kit, the specimen is attached to a cotton ball, and then the specimen is dissolved in the extraction solution by shaking the cotton ball in a flexible tube containing the extraction solution so that a swab is removed while pressing the tube and squeezing the cotton ball. Next, a cap having a nozzle is fastened to the tube, and the tube is turned over and compressed to provide the specimen dissolved in the extraction solution to the reading device through the cap. On the other hand, in the PCR (Polymerase Chain Reaction) test, a swab is placed in the tube containing the extraction solution, and then a certain part of the swab is cut with scissors. After that, the lid is closed, and the tube is transferred. The clinical pathologist concentrates the sample in the transferred tube and extracts RNA from it to read it. Until now, there has been no way for an automated reading device to process specimens collected from a swab.

There are two reasons why it is difficult for an automated reading device to process specimens collected from a swab. First, if there is a swab in the specimen container (tube), it is difficult for an automated reading device to collect a sample. The automated reading device collects specimens using a needle or pipet. In the case that the swab is loaded, unless the swab is aligned or fixed to one side, the collection hole may be blocked by the swab. Second, even in the case that there is no swab, if the specimen is collected out of the nasal cavity that has a lot of snot which is mucus, there is a possibility that the collection hole of the needle or pipet may be blocked by the snot.

In addition, in the case of field inspection, used swabs are problematic for disposal because of concerns about biohazards.

Technical Problems

Accordingly, the present invention provides a collection kit enabling an automated reading device to process the specimen collected by a swab.

In addition, the present invention further provides a collection kit without the risk of biohazard caused by swab.

In addition, the present invention further provides a collection kit easy to use for an automated reading device so as to reduce the effort of manpower and increase the inspection speed.

Technical Solutions

The present invention for achieving the above-mentioned objectives provides a collection kit for collecting a bio-sample using a collection rod, which comprises: a cap on the lower part of the central part of which a filter is detachably mounted, wherein a cover is formed on the upper part of the filter; a collection rod having a collection unit and a handle part; and a tube fastened with the cap and for accommodating the extraction solution.

Preferably, the tube accommodates the extraction solution and the collection rod together. And, the tube has an avoidance part formed on the inner surface thereof.

Preferably, the cap has a through hole formed in its periphery; and the handle part of the collection rod is inserted closely into the through hole. And, the cover is opened by external force.

Preferably, the collection rod has a cut groove formed on the handle part. And, the handle part has a stopper caught by the cap at the boundary of the collection unit. And, the collection rod has a sealing part on the top of the stopper.

Advantageous Effects

According to the present invention described above, there is no risk of biohazard caused by swab. In addition, a collection kit according to the present invention is easy to use for an automated reading device so as to reduce the effort of manpower and increase the inspection speed.

DETAILED DESCRIPTION OF EXEMPLARY EMBODIMENTS

Hereinafter, embodiments of the present invention will be described in detail with reference to the accompanying drawings. These embodiments are illustrative for the purpose of illustrating the present invention, and is not intended to limit the scope of the present invention.

Figure 1:
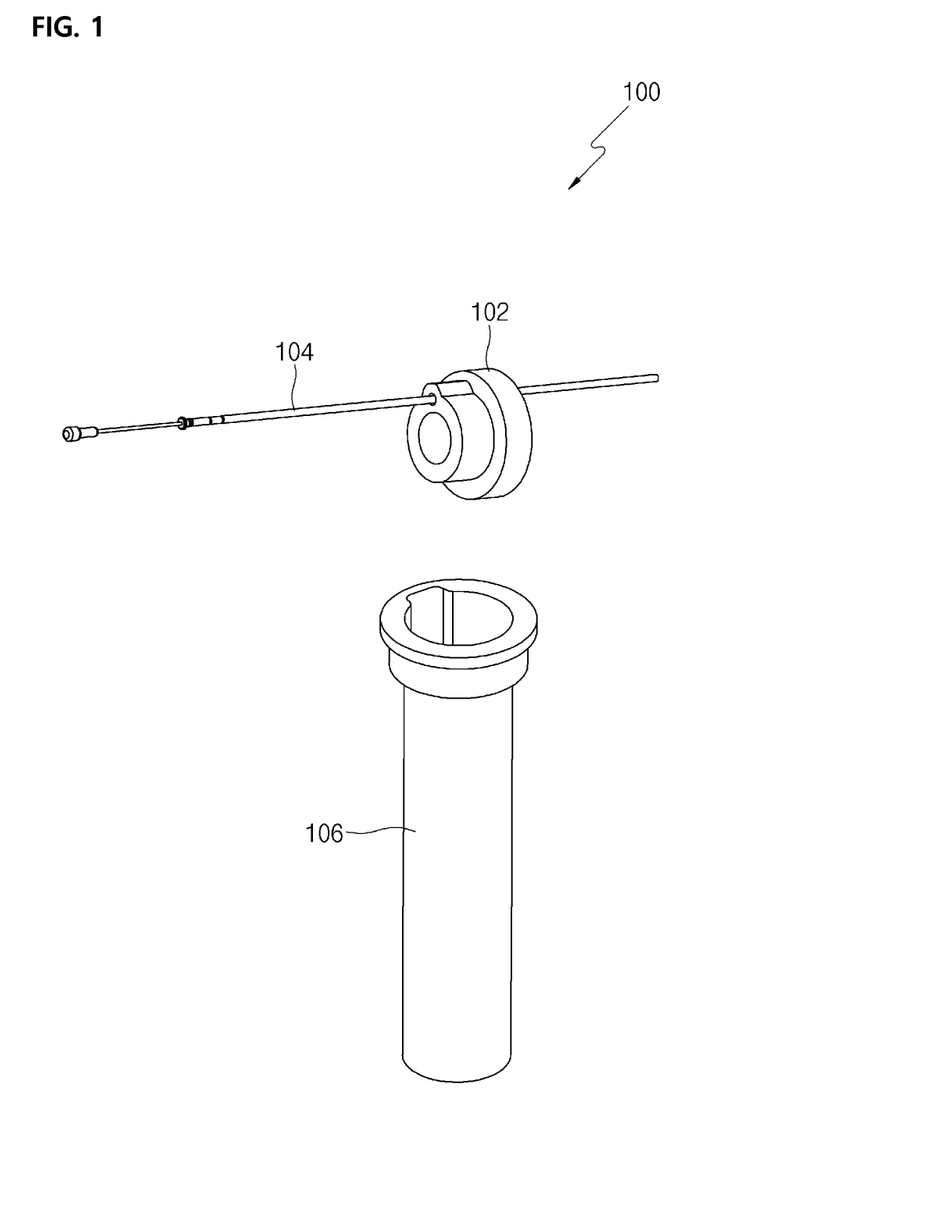
FIG. 1 depicts the configuration of a collection kit according to an embodiment of the present invention.

FIG. 1 depicts the configuration of a collection kit 100 according to an embodiment of the present invention. As shown in FIG. 1, the collection kit 100 according to this embodiment includes a cap 102, a collection rod 104, and a tube 106.

The collection kit 100 collects a bio-sample (or specimen) with a collection rod 104, and accommodates it in a tube 106 to which a cap 102 is fastened. Since the specimen and extraction solution are accommodated in the tube 106, the cap 102 is made of an elastic material for airtightness.

Figure 2:
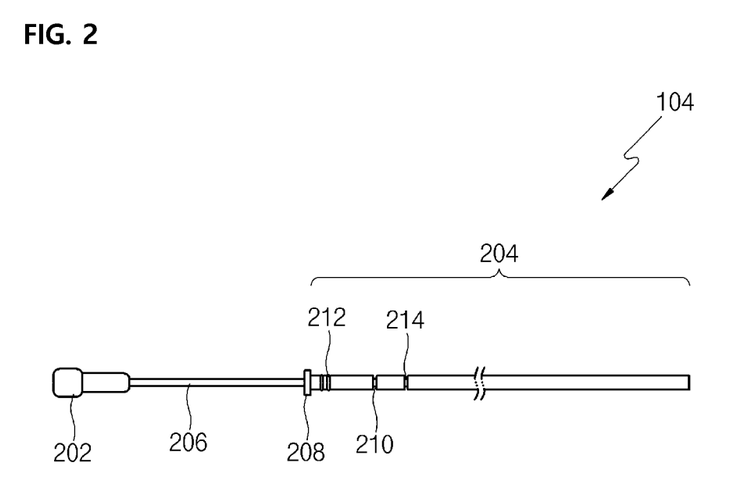
FIG. 2 shows a detailed configuration of a collection rod in the collection kit shown in FIG. 1.
Figure 3A:
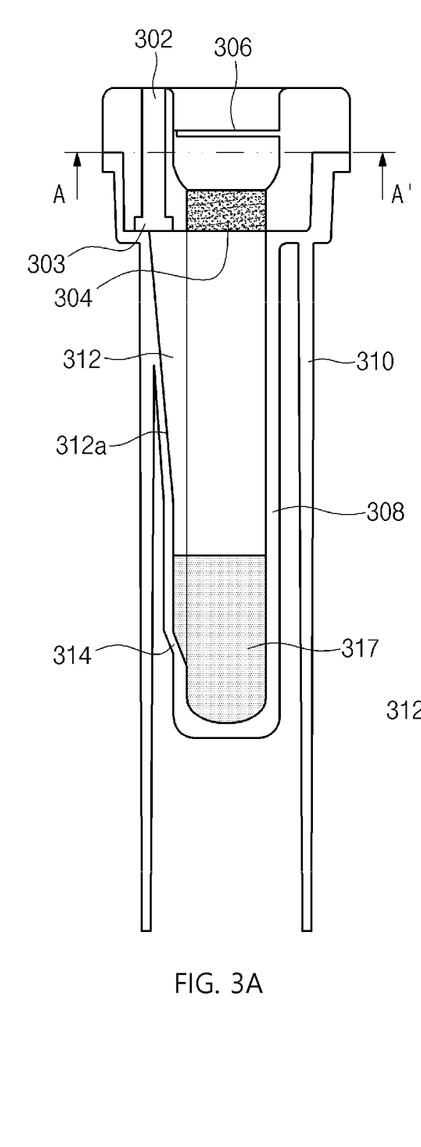
FIGS. 3A, 3B and 3C illustrate the coupling of a tube and a cap in the collection kit shown in FIG. 1.
Figure 3B:
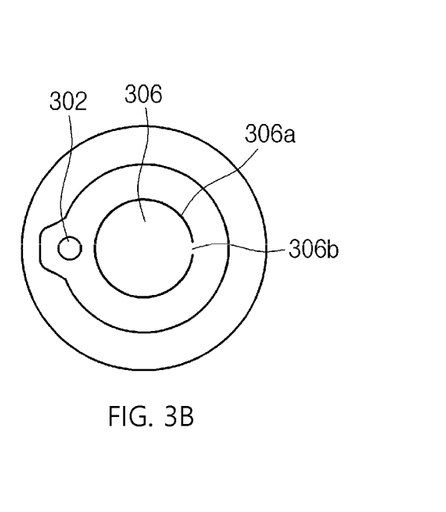
Figure 3C:
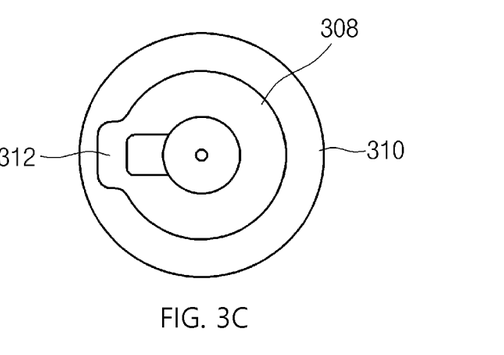

FIG. 2 shows a detailed configuration of a collection rod 104 in the collection kit 100 shown in FIG. 1. FIGS. 3A, 3B and 3C illustrate the coupling of a tube 106 and a cap 102 in the collection kit 100 shown in FIG. 1.

As shown in FIG. 2, the collection rod 104 is bar-shaped, has a collection unit 202 and a handle part 204, and is formed of a material that can be easily curved. A handle part 206 is formed between the collection unit 202 and the handle part 204. The handle part 206 allows the collection unit 202 to be positioned at the lower end of the tube 106 as the cap 102 and the tube 106 are fastened.

The handle part 204 has a stopper 208 at the boundary with the collection unit 202. The stopper 208 restricts the cap 102 from moving toward the collection unit 202.

A cut groove 210 is formed in the upper portion of the stopper 208 of the handle part 204. The cut groove 210 is formed approximately the length corresponding to the height of the cap 102 away from the stopper 208. When collecting the specimen, in order to properly collect the specimen, the length of the collection rod 104 inserted into the nose is required to be longer than the length of the tube 106. However, since the long collection rod 104 makes it difficult to transfer the collected specimen, the collection rod 104 is cut at the cut groove 210 to facilitate transfer. If the cut groove 210 is formed approximately the length corresponding to the height of the cap 102 away from the stopper 208, the length of the collection rod 104 protruding from the top surface of the cap 102 becomes very small when the collection rod 104 is cut at the cut groove 210.

A sealing part 212 is formed between the stopper 208 and the cut groove 210. The sealing part 212 prevents the extraction solution or specimen from leaking into the gap between the cap 102 and the collection rod 104. A depth line 214 is formed at an upper portion of the cut groove 206. The depth line 214 works as a reference line of the depth at which the collection rod 104 is inserted into the human body (eg, in the nose).

FIG. 3A is a side cross-sectional view showing that the cap 102 is fastened to the tube 106. FIG. 3B is a plan view seen from the dashed line A-A☐ shown in FIG. 3A. FIG. 3C is a bottom view.

The cap 102 is installed so that a filter 304 is detachably mounted on the lower portion of the central portion of the cap 102. A through hole 302 is formed on the periphery of the cap 102. The handle part 204 of the collection rod 104 is inserted into the through hole 302 with close contact. A locking groove 303 is formed at the lower end of the through hole 302. Since the collection rod 104 is inserted into the through hole 302 to be fixed on one side of the tube 106, interference of the collection rod 104 can be prevented when an automated reading device collects specimens with a needle, a pipet, a collection tip or the like. Since the cap 102 is formed of an elastic material such as rubber, airtightness is maintained between the through hole 302 and the collection rod 104.

A cover 306 is formed on the upper portion of the filter 304 (or the upper portion of the central portion of the cap 102). The cover 306 has an incision 306a and a non-incision 306b. The incision 306a is in the shape of a circle centered on the center of the cap 102, and is composed of a thin film except for the non-incision 306b, and is not cut during the collection and transfer process. The incision 306a is cut only when an automated reading device applies an external force such as compression of a collection tip or the like to it.

The tube 106 includes a vessel part 308 containing an extraction solution 307 for dissolving the specimen, and a body 310 to be mounted on a tube rack (not shown). The avoidance part 312 is formed in the form of a channel on one side on the inner surface of the vessel part 308 so as to reach to the bottom of the vessel part 308. The avoidance part 312 is adjacent to the through hole 302 as the cap 102 and the tube 106 are fastened. The avoidance part 312 is inclined toward the central part so as to guide the collection rod 104 to the lower central part of the vessel part 308.

The tube 106 has a slope part 314 at the lower part of the avoidance part 312. As the vessel part 308 passes the slope part 314 downward, the inner diameter of the vessel part 308 decreases. The slope part 314 allows the filter 304 to get in close contact with the inner surface of the vessel part 308 while the filter 304 is moving downward.

Figure 4A:
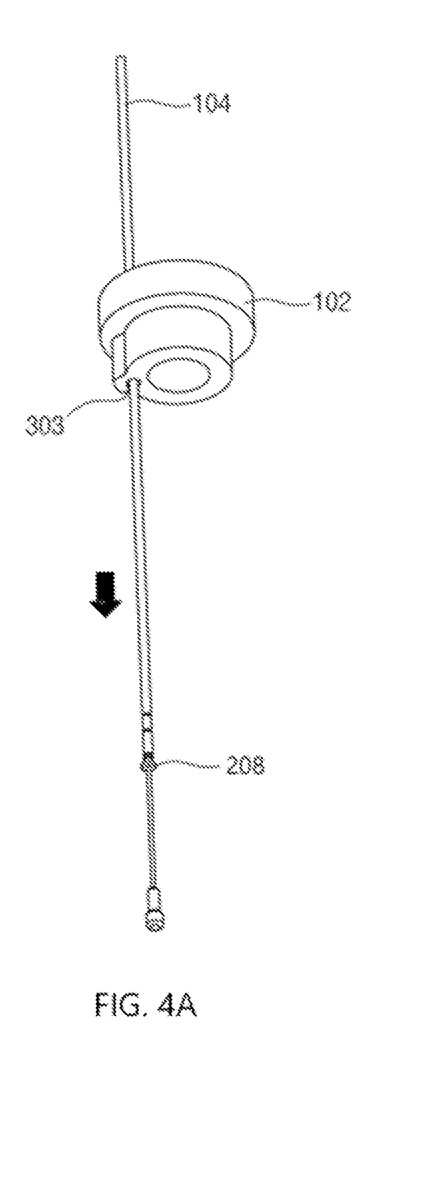
FIGS. 4A and 4B illustrate the positional relationship between the collection rod and the cap in the collection kit shown in FIG. 1.
Figure 4B:
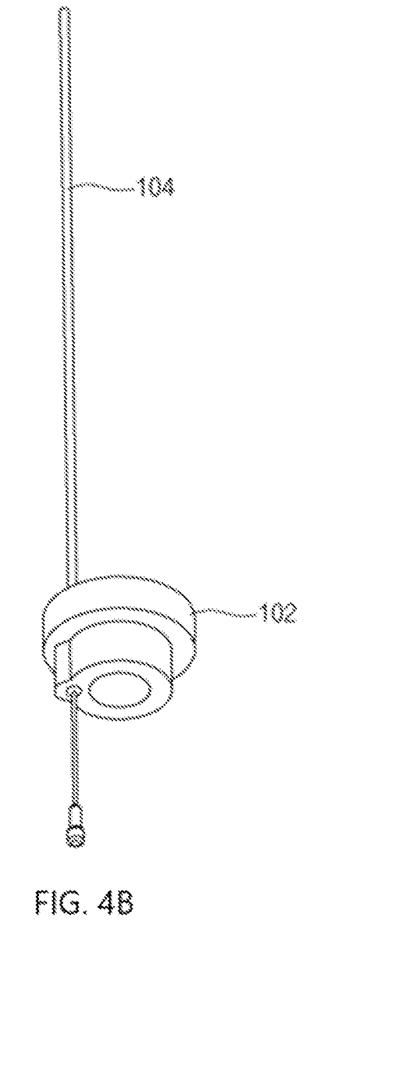

FIGS. 4a and 4b illustrate the positional relationship between the collection rod 104 and the cap 102 in the collection kit shown in FIG. 1.

FIG. 4A shows the position of the cap 102 as the specimen is collected using the collection rod 104. FIG. 4B shows the position of the cap 102 as the cap 102 is fastened to the tube 106. The cap 102 moves down along the collection rod 104 until the locking groove 303 reaches the stopper 212 of the collection rod 104.

When the collection rod 104 is inserted into the tube 106 along the avoidance part 312 after the cap 102 was moved down as shown in FIG. 4B, the collection rod 104 is curved along the slope of the avoidance part 312. When the collection rod 104 is inserted into the tube 106 with an appropriate depth using the depth line 214 and the cap 102 is fastened to the tube 104, the collection unit 202 to which the specimen is attached is located at the bottom of the vessel part 308. Then, the handle part 204 of the collection rod 104 is cut using the cut groove 210 and the collection kit 100 is transferred to an automated reading device (not shown). Because the cut handle part 204 has no specimen attached to it, there is no risk of biohazard so that it can be disposed of freely. The sealing part 212 prevents the extraction solution or specimen from leaking into the gap between the through hole 302 of the cap 102 and the collection rod 104 during the transfer process. Because the collection unit 202 that has the specimen attached to it is accommodated in the tube 106 and transferred, it is sufficiently dissolved by the extraction solution so that the reading device can extract more specimens.

Figure 5:
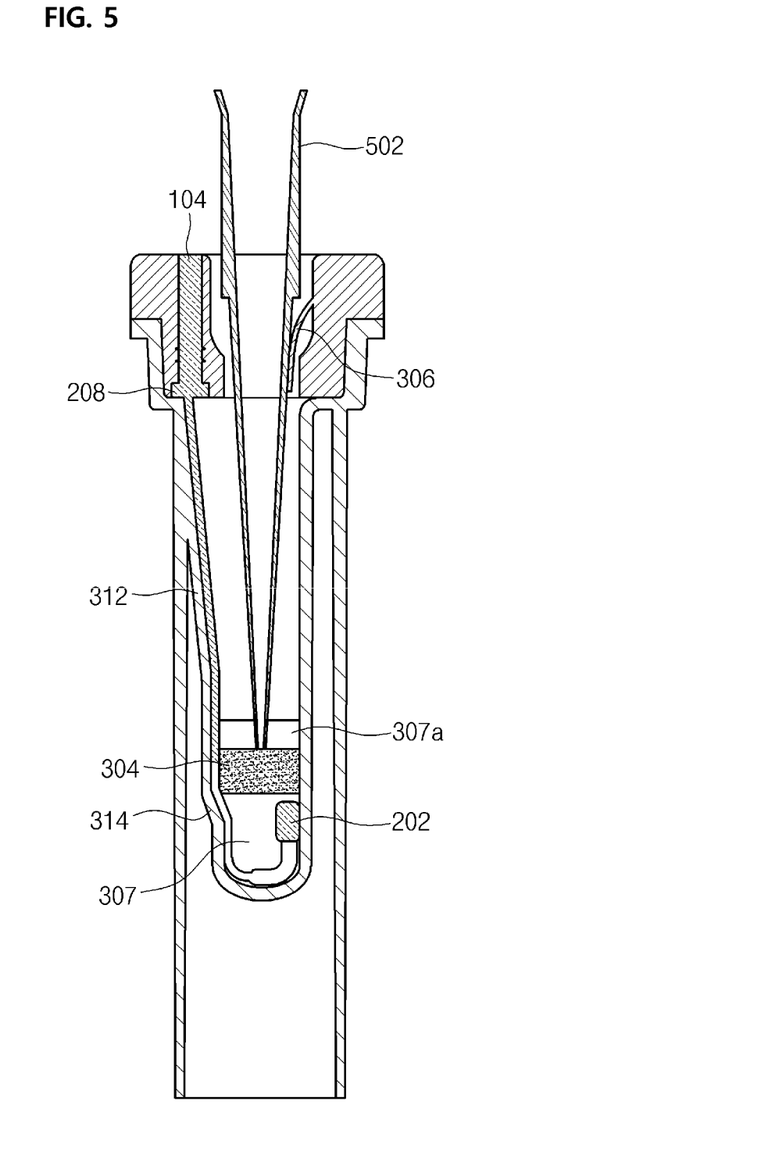
FIG. 5 is a side cross-sectional view illustrating how a specimen dissolved in an extraction solution is collected by a tip in the collection kit shown in FIG. 1.

FIG. 5 is a side cross-sectional view illustrating how a specimen dissolved in an extraction solution 307 is collected by a tip 502 in the collection kit 100 shown in FIG. 1. As shown in FIG. 5, the collection rod 104 is cut at the cut groove 210 and mounted on the automated reading device.

The collection tip 502 is mounted on an automated reading device (not shown) so that when the collection tip 502 presses on the cover 306, the incision 306a is cut. When the collection tip 502 is moved further downward by the reading device, the filter 304 installed in the lower portion of the central part of the cap 102 is moved to the slope part 314. The slope part 314 allows the filter 304 to be in close contact with the inner surface of the vessel part 308.

The specimen attached to the collection unit 202 is dissolved by the extraction solution 307. Snot in the extraction solution in which the specimen is dissolved is filtered by the filter 304. Only the upper extraction solution 307a passing through the filter 304 is collected by the collection tip 502. In this way, if the collection kit 100 is used, it does not require a separate pre-processing for specimen reading, so it is easy to use an automated reading device, reducing the effort of manpower and increasing the inspection speed.

If the distance of the stopper 212 from the collection unit 202 is too close, the specimen attached to the collection unit 202 may not be sufficiently immersed in the extraction solution 307, and a collection unit 202 may be located on the upper part of the the filter 304 moved downward by the collection tip 502. Unless the specimen is sufficiently immersed in the extraction solution 307, a part of the specimen is not dissolved in the extraction solution 307. When the collection unit 202 is located on the upper part of the filter 304, snot and the like may block the collection hole of the collection tip 502. If the stopper 212 is too far from the collection unit 202, the collection rod 104 may prevent the filter 304 from being sufficiently submerged in the extraction solution 307.

Figure 6:
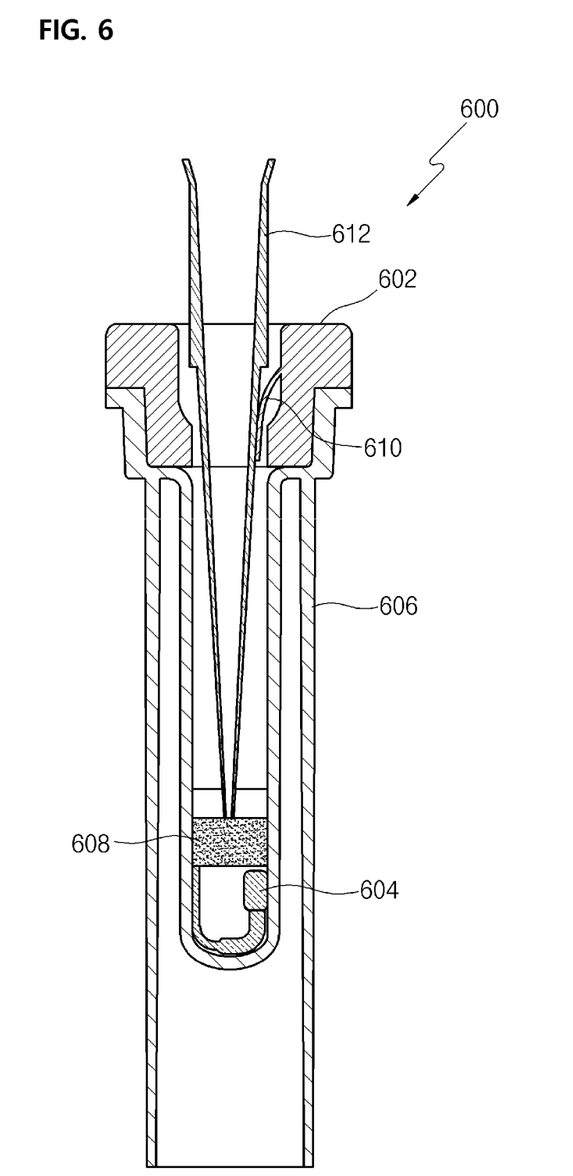
FIG. 6 is a side cross-sectional view illustrating how a specimen dissolved in an extraction solution is collected by a tip in the collection kit according to another embodiment of the present invention.

FIG. 6 is a side cross-sectional view illustrating how a specimen dissolved in an extraction solution is collected by a tip 612 in the collection kit 600 according to another embodiment of the present invention.

In the collection kit 600, the through hole into which the collection rod is inserted closely is not formed in the cap 602. Instead, a suitable point on the upper portion of the collection unit 604 in the collection rod is cut with scissors or the like so as to accommodate the collection unit 604 in the tube 606. When the tip 612 mounted on the reading device (not shown) applies an external force, the cover 610 is opened, and the tip 612 moves a filter 608 detachably mounted on the lower central part of the cap 602 to the lower part of the tube 606. The specimen attached to the collection unit 604 is dissolved by the extraction solution, filtered by the filter 608, and then collected by the collection tip 612.

Figure 7:
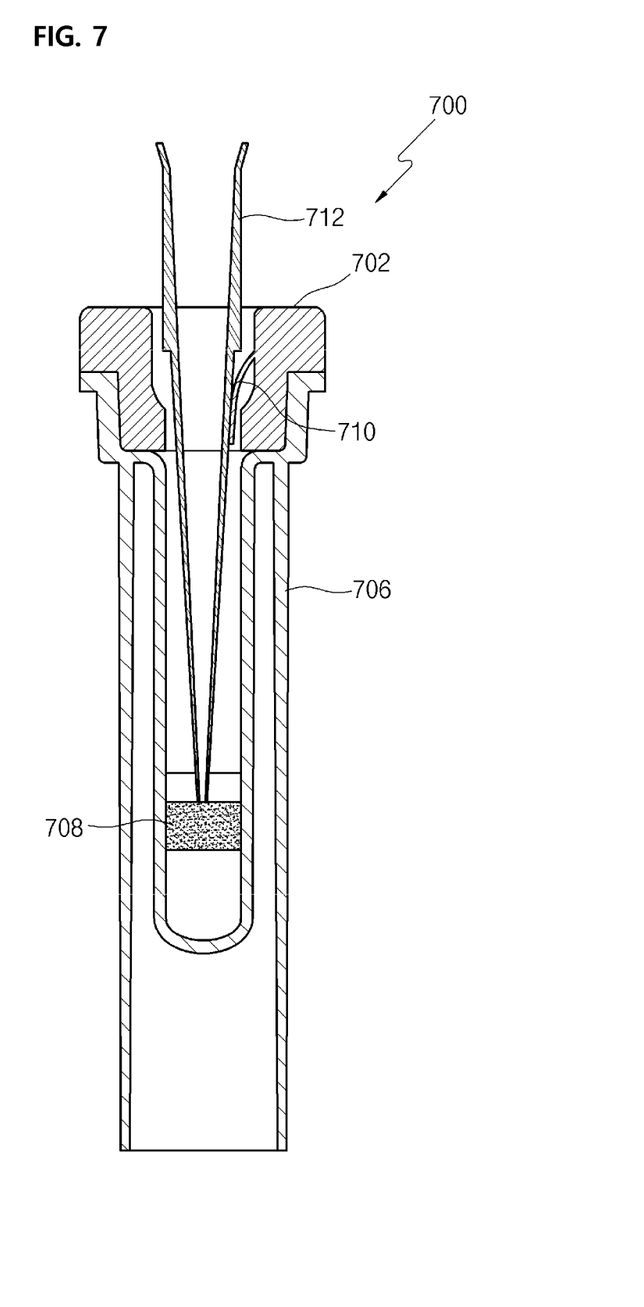
FIG. 7 is a side cross-sectional view illustrating how a specimen dissolved in an extraction solution is collected by a tip in the collection kit according to another embodiment of the present invention.

FIG. 7 is a side cross-sectional view illustrating how a specimen dissolved in an extraction solution is collected by a tip 712 in the collection kit 700 according to another embodiment of the present invention.

In the collection kit 700, a through hole into which the collection rod is inserted closely is not formed in the cap 702. The specimen attached to the collection unit is dissolved by the extraction solution accommodated in the tube 706, and the collection rod is immediately discarded. When the tip 712 mounted on the reading device (not shown) applies an external force, the cover 710 is opened, and the tip 712 moves a filter 708 detachably mounted on the lower central part of the cap 702 to the lower part of the tube 706. The specimen dissolved by the extraction solution is filtered by the filter 708, and then collected by the collection tip 712.

Although preferred embodiments of the present invention have been described in detail above, the scope of the present invention is not limited thereto, but various modifications and improvements made by those skilled in the art using the basic concept of the present invention as defined in the appended claims are also within the scope of the present invention.

What is claimed is:

1. A collection kit for collecting a bio-sample, comprising:
   a tube for accommodating an extraction solution;
   a cap configured to be fastened to the tube;
   a filter detachably mounted to the cap;
   wherein the cap comprises a cover above the filter, the cover is configured to be opened by a collection tip when the collection tip is pressed down toward the tube, and the filter is configured to be moved from the cap into a lower part of the tube by the collection tip.

2. The collection kit of claim 1, wherein the tube is configured to accommodate the extraction solution and at least a collection unit of a collection rod together.

3. The collection kit of claim 2, wherein the cap has a through hole formed proximate its periphery; and wherein the through hole is configured to receive a handle part of the collection rod.

4. The collection kit of claim 3, wherein the collection rod has a cut groove formed on the handle part, wherein the cut groove defines a location where the collection rod is capable of being cut.

5. The collection kit of claim 3, wherein the handle part has a stopper configured to restrict a movement of the cap towards the collection unit of the collection rod.

6. The collection kit of claim 3, wherein the collection rod has a sealing part configured to prevent the extraction solution from leaking between the through hole and the collection rod.

7. The collection kit of claim 2, wherein the tube has an avoidance part formed on an inner surface thereof, wherein the avoidance part guides the collection rod.

* * * * *